(12) United States Patent
Nishino et al.

(10) Patent No.: US 12,351,789 B2
(45) Date of Patent: Jul. 8, 2025

(54) METHOD FOR PRODUCING CELL LAMINATE

(71) Applicant: FUJIFILM CORPORATION, Tokyo (JP)

(72) Inventors: Masafumi Nishino, Kanagawa (JP); Koju Ito, Kanagawa (JP); Shinji Mima, Kanagawa (JP); Hayato Miyoshi, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 677 days.

(21) Appl. No.: 16/695,073

(22) Filed: Nov. 25, 2019

(65) Prior Publication Data

US 2020/0095531 A1 Mar. 26, 2020

Related U.S. Application Data

(63) Continuation of application No. PCT/JP2018/021930, filed on Jun. 7, 2018.

(30) Foreign Application Priority Data

Jun. 9, 2017 (JP) ................. 2017-114755

(51) Int. Cl.
 *C12M 1/12* (2006.01)
 *C12N 5/071* (2010.01)

(52) U.S. Cl.
 CPC ............ *C12M 25/14* (2013.01); *C12M 25/01* (2013.01); *C12M 25/06* (2013.01); *C12N 5/0602* (2013.01); *C12N 2513/00* (2013.01); *C12N 2533/90* (2013.01)

(58) Field of Classification Search
 CPC ...... C12M 25/14; C12M 25/02; C12M 25/06; C12N 5/0602; C12N 2513/00; C12N 2533/90
 USPC ....................................................... 435/395
 See application file for complete search history.

(56) References Cited

U.S. PATENT DOCUMENTS

| | | |
|---|---|---|
| 2006/0121606 A1 | 6/2006 | Ito et al. |
| 2010/0273200 A1 | 10/2010 | Niwa et al. |
| 2011/0003359 A1 | 1/2011 | Fujiyama et al. |
| 2013/0309677 A1 | 11/2013 | Blackman et al. |
| 2017/0037353 A1 | 2/2017 | Taki et al. |
| 2017/0044480 A1 | 2/2017 | Nakagawa et al. |

FOREIGN PATENT DOCUMENTS

| | | |
|---|---|---|
| CN | 1788080 A | 6/2006 |
| JP | 2002-335949 A | 11/2002 |
| JP | 2002335949 * | 11/2002 |
| JP | 2007-166915 A | 7/2007 |
| JP | 2009-213421 A | 9/2009 |
| JP | 5113332 B2 | 1/2013 |
| JP | 2015-516154 A | 6/2015 |
| JP | 2017-29092 A | 2/2017 |
| WO | 2009/099066 A1 | 8/2009 |
| WO | 2015/166625 A1 | 11/2015 |

OTHER PUBLICATIONS

English language translation of the following: Office action dated Sep. 9, 2020 from the KIPO in a Korean patent application No. 10-2019-7036033 corresponding to the instant patent application.
English language translation of the following: Office action dated Sep. 29, 2020 from the JPO in a Japanese patent application No. 2019-523979 corresponding to the instant patent application.
Office Action dated Feb. 17, 2022, issued by the EPO in corresponding EP Patent Application No. 18812595.9.
International Search Report issued in International Application No. PCT/JP2018/021930 on Augsut 14, 2018.
Written Opinion of the ISA issued in International Application No. PCT/JP2018/021930 on Aug. 14, 2018.
Extended European Search Report dated Mar. 6, 2020, issued in corresponding EP Patent Application No. 18812595.9.
Office action dated Nov. 26, 2020 from the CIPO in a Korean patent application No. 3,066,325 corresponding to the instant patent application.
Office action dated Nov. 26, 2020 from the CIPO in Canadian patent application No. 3,066,325 corresponding to the instant patent application.

(Continued)

*Primary Examiner* — Jennifer M. H. Tichy
(74) *Attorney, Agent, or Firm* — SOLARIS Intellectual Property Group, PLLC

(57) ABSTRACT

Provided is a method for producing a cell laminate including cell layers on both surfaces of a porous membrane, using a vessel having a bottom portion and a side wall portion standing from a periphery of the bottom portion, the porous membrane, and a holding member configured to hold the porous membrane such that the porous membrane faces an inner bottom surface of the vessel and is held at a position that does not contact the inner bottom surface, the method including culturing first cells in a liquid medium that contacts the inner bottom surface of the vessel and a surface of the porous membrane, in a state in which the porous membrane is held, by the holding member, at a position that does not contact the inner bottom surface of the vessel so as to face the inner bottom surface, and in which the bottom portion of the vessel is positioned at the upper side while the porous membrane is positioned at the lower side in a direction of gravity; and culturing the first cells at a lower surface of the porous membrane and culturing second cells at an upper surface of the porous membrane, in a state in which the porous membrane is held, by the holding member, at a position that does not contact the inner bottom surface of the vessel so as to face the inner bottom surface, and in which the bottom portion of the vessel is positioned at the lower side while the porous membrane is positioned at the upper side in the direction of gravity.

8 Claims, 7 Drawing Sheets

(56) References Cited

OTHER PUBLICATIONS

Office action dated Sep. 29, 2021 from the IPO in a Indian patent application No. 201947050145 corresponding to the instant patent application.

English language translation of the following: Office action dated Dec. 2, 2022 from the SIPO in a Chinese patent application No. 201880037633.6 corresponding to the instant patent application. This office action translation is submitted now in order to supplement the understanding cited references disclosed in the instant Information Disclosure Statement.

Office action dated Jul. 4, 2023 from the IPO in a Indian patent application No. 201947050145 corresponding to the instant patent application.

English language translation of the following: Office action dated Apr. 18, 2023 from the SIPO in a Chinese patent application No. 201880037633.6 corresponding to the instant patent application.

* cited by examiner (A)

(B)

Track-etched Membrane

Honeycomb Membrane

HUVEC (CD31)

HUASMC
($\alpha$-smooth muscle actin)

METHOD FOR PRODUCING CELL LAMINATE

CROSS-REFERENCE TO RELATED APPLICATION

This application is a continuation application of International Application No. PCT/JP2018/021930, filed Jun. 7, 2018, the disclosure of which is incorporated herein by reference in its entirety. Further, this application claims priority from Japanese Patent Application No. 2017-114755, filed Jun. 9, 2017, the disclosure of which is incorporated herein by reference in their entirety.

BACKGROUND OF THE INVENTION

1. Field of the Invention

The present disclosure relates to a method for producing a cell laminate.

2. Description of the Related Art

A method for producing an artificial cellular tissue having a structure similar to that of a tissue in a living organism is disclosed in, for example, JP2002-335949A and JP5113332B.

JP2002-335949A discloses that cells are cultured on both surfaces of a honeycomb structure film to obtain a three-dimensional aggregate of the cells. That is, JP2002-335949A discloses that the same type of cells (hepatocytes or cardiomyocytes) are cultured on both surfaces of the honeycomb structure film in such a manner that cells are seeded on one surface of the film and allowed to adhere to the film, and then cells are seeded on the other surface of the film.

JP5113332B discloses a blood-brain barrier model in which a brain capillary endothelial cell layer is disposed on an upper surface of a filter of a filter device which is referred to as a "cell culture insert", a brain pericyte layer is disposed on a lower surface of the filter, and an astrocyte layer is disposed at the bottom surface of a culture plate. In this disclosure, cell layers are formed on both surfaces of the filter in such a manner that, in a state where the cell culture insert is turned upside down, brain pericytes are seeded and cultured on the filter, then the cell culture insert is placed in the culture plate, and the vascular endothelial cells are seeded inside the cell culture insert.

SUMMARY OF THE INVENTION

In order to obtain an artificial cellular tissue for evaluating drugs or disease states, which could replace animal testing, it is necessary to construct a cellular tissue having a structure and a function similar to those of a tissue in a living organism. From the viewpoint of constructing a cellular tissue having a structure and a function similar to those of a tissue in a living organism, it is preferable to culture cells on both surfaces of a porous membrane having a high aperture ratio, such as a honeycomb structure film in JP2002-335949A, which serves as a scaffold for cell culture. In addition, it is also required to construct a cell laminate in which different types of cells are cultured on both surfaces of the porous membrane in accordance with the living tissue to be mimicked by an artificial cellular tissue, so that the cell types are different in both cell layers.

However, JP2002-335949A does not specifically disclose a method of culturing different types of cells on both surfaces of the honeycomb structure film.

On the other hand, JP5113332B discloses a method of culturing different types of cells on upper and lower surfaces of a filter of a cell culture insert. The cell culture insert used in this culturing method is a Transwell (registered trademark) insert, and the filter thereof is a track-etched membrane (TE membrane). Since the TE membrane generally has a low aperture ratio (about 2% to 20%), a liquid medium is difficult to fall through the TE membrane even in a case where a cell suspension is placed on the TE membrane. Therefore, in a case where it is a cell culture insert comprising a TE membrane as a filter, cell culture can be carried out by seeding a cell suspension on the filter in a state where the cell culture insert is turned upside down. However, in a case where a porous membrane having a high aperture ratio, such as the honeycomb structure film in JP2002-335949A, is applied to the filter of the cell culture insert, and then in a case where the cell suspension is seeded on the filter in a state where the cell culture insert is turned upside down, cell culture cannot be carried out because the liquid medium falls through the pores of the porous membrane.

The embodiment of the present disclosure has been made in view of the above circumstances.

The present disclosure aims to provide a novel method for producing a cell laminate, which is an object to be achieved by the present disclosure.

Specific means for achieving the above object include the following aspects.

[1] A method for producing a cell laminate comprising cell layers on both surfaces of a porous membrane, using a vessel having a bottom portion and a side wall portion standing from a periphery of the bottom portion, the porous membrane, and a holding member configured to hold the porous membrane such that the porous membrane faces an inner bottom surface of the vessel and is held at a position that does not contact the inner bottom surface, the method comprising:

culturing first cells in a liquid medium that contacts the inner bottom surface of the vessel and a surface of the porous membrane, in a state in which the porous membrane is held, by the holding member, at a position that does not contact the inner bottom surface of the vessel so as to face the inner bottom surface, and in which the bottom portion of the vessel is positioned at the upper side while the porous membrane is positioned at the lower side in a direction of gravity; and culturing the first cells at a lower surface of the porous membrane and culturing second cells at an upper surface of the porous membrane, in a state in which the porous membrane is held, by the holding member, at a position that does not contact the inner bottom surface of the vessel so as to face the inner bottom surface, and in which the bottom portion of the vessel is positioned at the lower side while the porous membrane is positioned at the upper side in the direction of gravity.

[2] The method for producing a cell laminate according to [1], in which the inner bottom surface of the vessel has a property that the first cells do not adhere.

[3] The method for producing a cell laminate according to [1] or [2], in which the holding member comprises:

a cylindrical portion configured to hold the porous membrane at one axial-direction end of the cylindrical portion, the cylindrical portion having a smaller outer diameter than an inner diameter of the vessel, and a length of the cylindrical portion in the axial direction being shorter than a height of the side wall portion of the vessel; and a protruding portion protruding outwardly in a radial direction from the other axial-direction end of the cylindrical portion, the protruding portion being configured to engage with an edge of the side wall portion of the vessel.

[4] The method for producing a cell laminate according to any one of [1] to [3], in which the porous membrane is a porous membrane having a honeycomb structure.

[5] The method for producing a cell laminate according to any one of [1] to [4], in which a material of the porous membrane is at least one selected from the group consisting of polybutadiene, polystyrene, polycarbonate, polylactic acid, and a polylactic acid-polyglycolic acid copolymer.

[6] The method for producing a cell laminate according to any one of [1] to [5], in which, in the porous membrane, at least the surface on which the cells are cultured is coated with at least one selected from the group consisting of fibronectin, collagen, laminin, vitronectin, gelatin, perlecan, nidogen, proteoglycan, osteopontin, tenascin, nephronectin, a basement membrane matrix, and polylysine.

[7] The method for producing a cell laminate according to any one of [1] to [6], in which the first cells and the second cells are different types of cells, and the two types of cells of the first cells and the second cells are two types of cells selected from the group consisting of parenchymal cells, stromal cells, myocytes, fibroblasts, nerve cells, endothelial cells, epithelial cells, and cells capable of differentiating into any of these cells.

[8] The method for producing a cell laminate according to any one of [1] to [7], in which the first cells are smooth muscle cells or cells capable of differentiating into smooth muscle cells, and the second cells are vascular endothelial cells or cells capable of differentiating into vascular endothelial cells.

According to the present disclosure, provided is a novel method for producing a cell laminate.

DESCRIPTION OF THE PREFERRED EMBODIMENTS

Figure 1A:
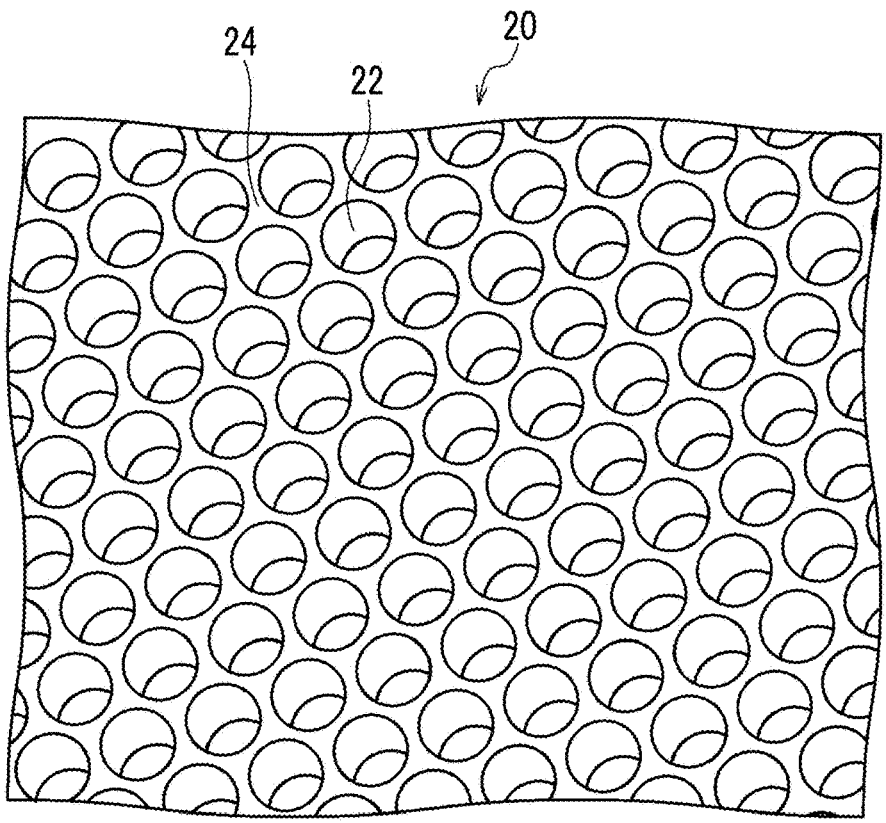
FIG. 1A is a perspective view showing an example of a porous membrane having a honeycomb structure.

Hereinafter, embodiments of the present invention will be described. The description and the working examples provided below illustrate exemplary embodiments, and do not limit the scope of the invention. The working mechanisms described in the present disclosure include presumptions, and whether or not the presumptions are correct does not limit the scope of the invention.

In the present disclosure, each numerical range indicated using "to" refers to a range including numerical values noted before and after the "to" as the lower limit value and the upper limit value, respectively.

In a case where a plurality of substances, each corresponding to a particular component in a composition, are present, the amount of the particular component in the composition described in the present disclosure means the total amount of the plurality of substances present in the composition, unless otherwise specified.

<Method for Producing Cell Laminate>

The method for producing a cell laminate according to the present disclosure is a method for producing a cell laminate comprising cell layers on both surfaces of a porous membrane by culturing cells on both surfaces of the porous membrane to form cell layers on both surfaces of the porous membrane.

The method for producing a cell laminate according to the present disclosure is carried out using a vessel having a bottom portion and a side wall portion standing from the periphery of the bottom portion, a porous membrane, and a holding member configured to hold the porous membrane such that the porous membrane faces the inner bottom surface of the vessel and is held at a position that does not contact the inner bottom surface. The vessel is hereinafter referred to as a "culture vessel".

Using a culture vessel, a porous membrane, and a holding member, the method for producing a cell laminate according to the present disclosure produces a cell laminate comprising cell layers on both surfaces of a porous membrane by culturing cells on both surfaces of the porous membrane.

First, the culture vessel, the porous membrane, and the holding member used in the production method of the present disclosure will be described.

[Culture Vessel]

The culture vessel is, for example, a dish, a multi-dish, or a multi-well plate. The shape of the bottom portion of the culture vessel is, for example, circular, rectangular, or square. The material of the culture vessel is, for example, polystyrene, polycarbonate, polyester, or glass. The culture vessel preferably has high transparency.

The inner bottom surface of the culture vessel is preferably flat. The inner bottom surface of the culture vessel preferably has a property such that cells do not adhere to the inner bottom surface. Thus, it is preferable that the inner bottom surface of the culture vessel has not been subjected to a corona discharge treatment or a protein coating treatment. The inner bottom surface of the culture vessel may be coated with, for example, a polymer having a phosphorylcholine group, a polyethylene glycol, or a hydrogel, in order to reduce adhesion of cells. Similar to the inner bottom surface, the inner side surface of the culture vessel preferably has a property such that cells do not adhere to the inner side surface.

[Porous Membrane]

In the production method of the present disclosure, the porous membrane is a scaffold on which the cells adhere and proliferate. The porous membrane used in the production method of the present disclosure is not limited in the production method, material, and shape thereof.

Examples of the method for producing a porous membrane include a production method in which through-holes are formed by carrying out etching, blasting or punching on a membrane made of a resin to produce a porous membrane; and production methods in which through-holes are formed by allowing water droplets to grow in a coating film containing a polymer and a solvent, which are disclosed in JP4734157B, JP4945281B, JP5405374B, JP5422230B, and JP2011-074140A.

Examples of the material of the porous membrane include polymers such as polybutadiene, polystyrene, polycarbonate, polyesters (for example, polylactic acid, polycaprolactone, polyglycolic acid, polylactic acid-polyglycolic acid copolymer, polylactic acid-polycaprolactone copolymer, polyethylene terephthalate, polyethylene naphthalate, polyethylene succinate, polybutylene succinate, and poly-3-hydroxybutyrate), polyacrylate, polymethacrylate, polyacrylamide, polymethacrylamide, polyvinyl chloride, polyvinylidene chloride, polyvinylidene fluoride, poly-hexafluoropropene, polyvinyl ether, polyvinylcarbazole, polyvinyl acetate, polytetrafluoroethylene, polylactone, polyamide, polyimide, polyurethane, polyurea, polyaromatics, polysulfone, polyethersulfone, polysiloxane derivatives, and cellulose acylate (for example, triacetyl cellulose, cellulose acetate propionate, and cellulose acetate butyrate). Polymers that dissolve in a hydrophobic organic solvent are preferable from the viewpoint of producing a porous membrane using the production method disclosed, for example, in JP4734157B. These polymers may have the form of a homopolymer, a copolymer, a polymer blend, or a polymer alloy, as necessary, from the viewpoints of, for example, solubility in solvents, optical properties, electrical properties, membrane strength, and elasticity. These polymers may be used singly or in combination of two or more thereof.

As the material of the porous membrane, polybutadiene, polyurethane, polystyrene, or polycarbonate is preferred from the viewpoint of self-supporting properties, and polylactic acid, a polylactic acid-polyglycolic acid copolymer, or a polylactic acid-polycaprolactone copolymer is preferred from the viewpoint of easily maintaining the engraftment of the cell layers.

From the viewpoint of cell adhesion property, in the porous membrane, at least the surface of the region where cells are seeded is preferably coated with at least one selected from the group consisting of fibronectin, collagen (for example, type I collagen, type IV collagen, or type V collagen), laminin, vitronectin, gelatin, perlecan, nidogen, proteoglycan, osteopontin, tenascin, nephronectin, a basement membrane matrix, and polylysine. With respect to the basement membrane matrix, commercial products (for example, MATRIGEL (registered trademark) and GELTREX (registered trademark)) are available. In the porous membrane, the interior of the pores is also preferably coated with at least one of these materials.

The porous membrane preferably has a honeycomb structure. The honeycomb structure in the present disclosure refers to a structure that is partitioned into a large number of through-holes by partition walls.

In a case where the porous membrane of the present disclosure has a honeycomb structure, the through-holes of the honeycomb structure are opened toward the main surface of the porous membrane. In a case where the porous membrane of the present disclosure has a honeycomb structure, a plurality of honeycomb structures may be stacked.

In the present disclosure, the shape of the through-holes of the honeycomb structure is not limited. The shape of the through-holes is, for example, a truncated sphere shape that lacks a part of a sphere, a barrel shape, a circular column shape, or a prismatic column shape, and through-holes in plural types of shapes may be present together. The shape of the openings of the through-holes is, for example, a circular shape, an ellipsoidal shape, or a polygonal shape, and openings in plural types of shapes may be present together. In the honeycomb structure, adjacent through-holes may partially communicate with one another.

The through-holes in the porous membrane having a honeycomb structure are preferably arranged regularly from the viewpoint of increasing the homogeneity of the cell layer formed on the porous membrane. The regular arrangement may include a break or shift. However, the regular arrangement preferably includes continuous repetitions without any gaps, in all directions.

Hereinafter, an embodiment of a porous membrane having a honeycomb structure will be described with reference to the accompanying drawings. In each drawing, the same or equivalent element or portion is assigned the same reference numeral. In the description below, the "longer diameter" refers to the longest length between any two points on an outline, or, in a case in which the direction is specified, refers to the longest distance between any two points in the specified direction.

Figure 1B:
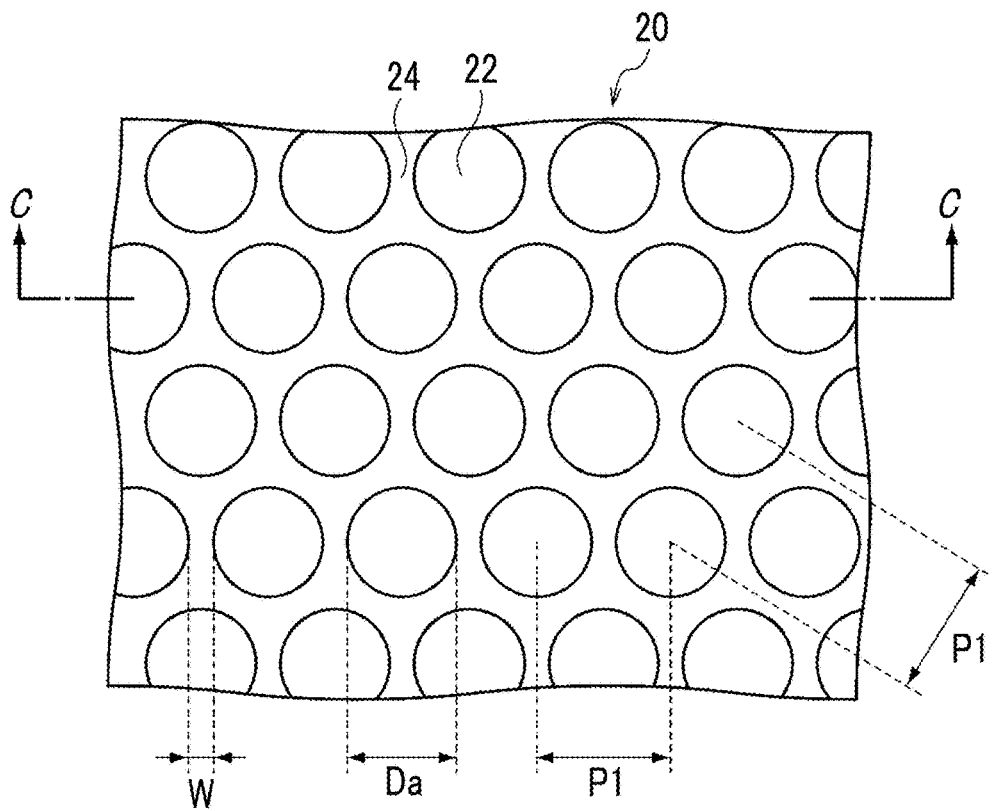
FIG. 1B is a plan view of the porous membrane in FIG. 1A as viewed from an upper surface side.
Figure 1C:
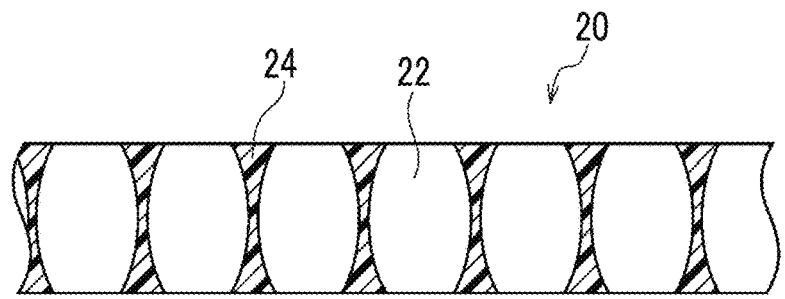
FIG. 1C is a cross-sectional view taken along a line c-c of the porous membrane in FIG. 1B.

A porous membrane 20, which is one example of the porous membrane having a honeycomb structure, is illustrated in FIGS. 1A to 1C. FIG. 1A is a perspective view of the porous membrane 20, FIG. 1B is a plan view of the porous membrane 20 in FIG. 1A viewed from the upper surface side, and FIG. 1C is a cross-sectional view of the porous membrane 20 taken along a line c-c in FIG. 1B.

Through-holes 22 are arranged over the entire area on a main surface of the porous membrane 20. However, in a case where there is a region on the porous membrane 20 that cannot be contacted by cells, through-holes 22 may not be disposed in the region. In the porous membrane 20, adjacent through-holes 22 are separated from one another by partition walls 24.

The arrangement of the through-holes 22 is an arrangement in which a parallel hexagon (preferably a regular hexagon) or a similar shape serves as a unit, and in which the center of an opening is positioned at the vertices of the shape and the intersections of diagonal lines. The "center of an opening" refers to the center of gravity of the two-dimensional shape of the opening on the main surface.

The shape of the through-holes 22 is, for example, a truncated sphere shape that lacks a part of a sphere, a barrel shape, a circular column shape, or a prismatic column shape. The shape of the openings of the through-holes 22 is, for example, a circular shape, an ellipsoidal shape, or a polygonal shape. Adjacent through-holes 22 may communicate with one another by communication holes in the interior of the porous membrane 20.

Hereinafter, the dimension of the porous membrane 20 will be described.

The pitch P1 of the through-holes 22 is the distance between the centers of adjacent openings. The pitch P1 is preferably set in accordance with the sizes of the cells cultured on the porous membrane 20. The pitch P1 is, for example, 1 μm to 50 μm.

The opening diameter Da is the longer diameter of the opening of the through-hole 22. The opening diameter Da is preferably a size that allows the cells to be seeded to be retained on the porous membrane 20. The opening diameter Da is, for example, 10% to 150% of the longer diameter (for example, 10 μm to 50 μm) of the cells to be seeded. In a case where a vascular wall model is constructed in order to carry out an erythrocyte leakage test, the opening diameter Da is preferably a size that allows erythrocytes to pass through. The opening diameter Da is preferably not excessively small from the viewpoint of allowing a cell-cell contact between cells on one surface and cells on the other surface. On the other hand, the opening diameter Da is preferably not excessively large from the viewpoint of the strength of the porous membrane 20. From these viewpoints, the opening diameter Da is preferably 1 μm to 20 μm, more preferably 2 μm to 10 μm, and still more preferably 3 μm to 5 μm.

The coefficient of variation of the opening diameter Da is preferably 20% or less, and a smaller coefficient of variation is more preferred. A smaller coefficient of variation of the opening diameter Da provides a higher homogeneity of the cell layers formed on the porous membrane 20. The coefficient of variation is a value obtained by dividing a standard variation of a certain group by an arithmetic mean value of the group, and the coefficient of variation is an index of the degree of variations within the group. In the present disclosure, the coefficient of variation is expressed in percentage.

The width W of the partition wall 24 refers to the length of the width of the partition wall 24 that is measured between the centers of adjacent openings. The width W is preferably a width that allows the cells to be seeded to be retained on the porous membrane 20.

The aperture ratio of the porous membrane 20 is preferably 30% to 70%, more preferably 35% to 65%, and still more preferably 40% to 60%, from the viewpoints of substance permeability and the strength of the porous membrane. The aperture ratio of the porous membrane 20 is the ratio of the total area of the openings to the area of the main surface (area including the openings) in a plan view. The aperture ratio is calculated individually for one surface and the other surface.

The membrane thickness of the porous membrane 20 is preferably not excessively large from the viewpoint of allowing cell-cell contact between cells on one surface and cells on the other surface. The membrane thickness of the porous membrane 20 is preferably not excessively small from the viewpoint of the strength of the porous membrane 20. From these viewpoints, the membrane thickness of the porous membrane 20 is preferably 0.5 μm to 40 μm, more preferably 1 μm to 20 μm, and still more preferably 2 μm to 8 μm.

Details of the production method of the porous membrane 20 are described in, for example, JP4734157B, JP4945281B, JP5405374B, JP5422230B, and JP2011-74140A.

In the method for producing a cell laminate according to the present disclosure, the porous membrane is a scaffold to which cells adhere and proliferate. A higher aperture ratio of the porous membrane and a smaller membrane thickness of the porous membrane each provide at least one of a more active cell-cell interaction, that is, signal transduction by soluble factors, between cells on one surface and cells on the other surface, or a more active cell-cell contact between cells on one surface and cells on the other surface. A more active cell-cell interaction during cell culture enables the production of a cell laminate having a function more close to that of a tissue in a living organism. From this viewpoint, the porous membrane used in the production method of the present disclosure is preferably a porous membrane having a honeycomb structure, and the porous membrane 20 is one of the preferable forms.

[Holding Member]

The holding member is a member configured to hold the porous membrane such that the porous membrane faces the inner bottom surface of the culture vessel and is held at a position that does not contact the inner bottom surface.

The material of the holding member is preferably a resin such as polycarbonate, polystyrene, or polyester, from the viewpoints of high transparency, chemical stability in liquid media, and light weight.

The shape of the holding member is not limited. The holding member includes, for example, a portion configured to hold the porous membrane and a portion configured to contact the culture vessel. The holding member is, for example, a wire-shaped member, bar-shaped member or cylindrical member that comprises a protruding portion engaging with the edge of the side wall portion of the culture vessel.

With respect to the morphology of the holding member, the holding member is, for example, a member comprising a cylindrical portion configured to hold a porous membrane at one axial-direction end of the cylindrical portion, and a protruding portion protruding outwardly in the radial direction from the other axial-direction end of the cylindrical portion. Hereinafter, this embodiment will be described with reference to the drawings.

Figure 2A:
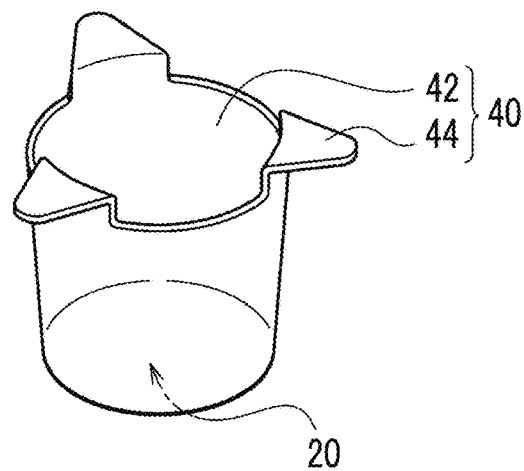
FIG. 2A is a perspective view showing an example of a holding member.
Figure 2B:
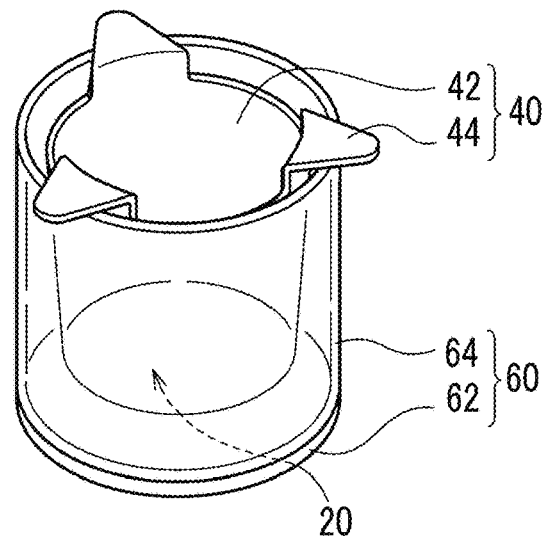
FIG. 2B is a perspective view showing a state where the holding member shown in FIG. 2A is installed in a culture vessel.

In FIG. 2A, a holding member 40, which is one example of the holding member, is illustrated in a state in which the holding member 40 comprises the porous membrane 20 (one example of the porous membrane). FIG. 2A is a perspective view of the holding member 40. FIG. 2B is a perspective view illustrating a state in which the holding member 40 comprising the porous membrane 20 is installed in a culture vessel 60 (one example of the culture vessel).

The holding member 40 comprises a cylindrical portion 42 and a protruding portion 44. The porous membrane 20 is disposed at one axial-direction end of the cylindrical portion 42. The porous membrane 20 has a size that at least closes the opening positioned at one end of the cylindrical portion 42. The porous membrane 20 is adhered to one end of the cylindrical portion 42 by thermal compression bonding, ultrasonic welding, laser welding, an adhesive, or a double-sided tape. Alternatively, the porous membrane 20 is fixed to one end of the cylindrical portion 42 by a ring-shaped fixing member that fits into the outer surface of the cylindrical portion 42.

The cylindrical portion 42 has an outer diameter smaller than the inner diameter of the culture vessel 60, and is insertable into the inside of the culture vessel 60 (that is, the space defined by the bottom portion 62 and the side wall portion 64). The length of the cylindrical portion 42 in the axial direction is shorter than the height of the side wall portion 64 of the culture vessel 60. Therefore, the porous membrane 20 does not contact the bottom portion 62 of the culture vessel 60.

The cylindrical portion 42 has a wall that is continuous in the circumferential direction and the axial direction. This configuration enables a liquid to be stored in the space defined by the porous membrane 20 and the cylindrical portion 42. However, a slit may be provided in the wall of the cylindrical portion 42 at a position near the protruding portion 44. The shape of the inner surface of the cylindrical portion 42 is, for example, a circular column shape, a prismatic column shape, a circular truncated cone shape, or a truncated pyramid shape.

The protruding portion 44 protrudes outwardly in the radial direction of the cylindrical portion 42 at an axial-direction end of the cylindrical portion 42 opposite from an end at which the porous membrane 20 is disposed. For example, three protruding portions 44 are provided with an interval of about 120° in the circumferential direction of the cylindrical portion 42. However, the number and the shape of the protruding portion 44 are not limited thereto. The protruding portion 44 may have the shape of a ring that is continuous in the circumferential direction of the cylindrical portion 42.

The protruding portion 44 has a protrusion length such that the protruding portion 44 engages with the edge of the side wall portion 64 of the culture vessel 60 in a case where the holding member 40 is inserted into the inside of the culture vessel 60. The holding member 40 is locked to the edge of the side wall portion 64 of the culture vessel 60 by the protruding portion 44.

The culture device having a shape as illustrated in FIG. 2A is generally called a cell culture insert.

Next, the steps in the production method of the present disclosure will be described. In the present disclosure, the scope of the term "step" includes an independent step as well as a step that cannot be clearly distinguished from other steps but still achieves the desired object of the step of interest.

Figure 3:
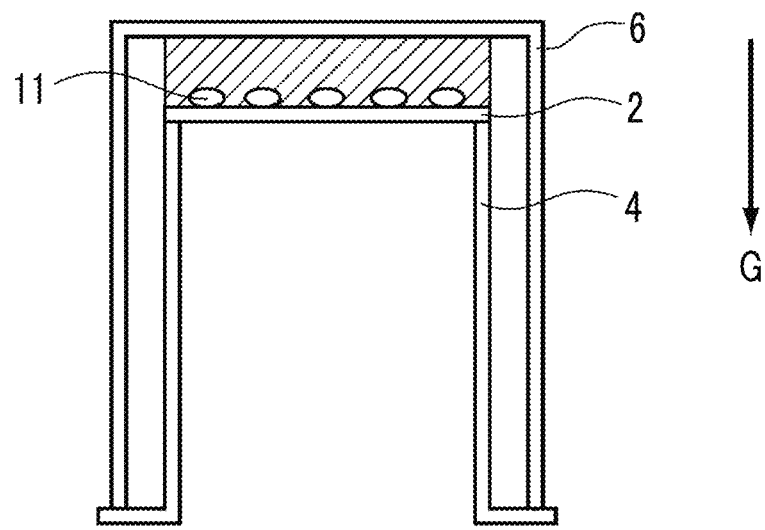
FIG. 3 is a schematic diagram showing an example of a production method of the present disclosure.
Figure 3:
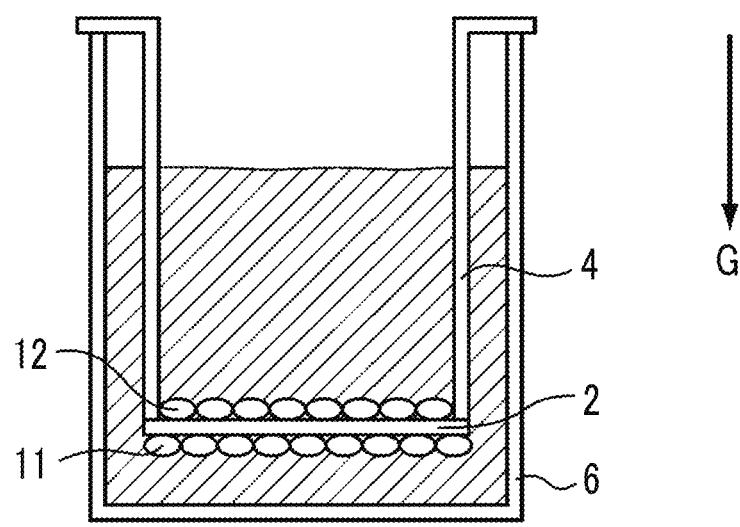

The method for producing a cell laminate according to the present disclosure includes the following steps (A) and (B). FIG. 3 is a schematic diagram illustrating one example of the production method of the present disclosure, and is a schematic diagram for explaining the steps (A) and (B). In FIG. 3, the arrow G indicates the direction of gravity.

Step (A): culturing first cells 11 in a liquid medium that contacts an inner bottom surface of a culture vessel 6 and a surface of a porous membrane 2, in a state in which the porous membrane 2 is held, by a holding member 4, at a position that does not contact the inner bottom surface of the culture vessel 6 so as to face the inner bottom surface, and in which the bottom portion of the culture vessel 6 is positioned at the upper side while the porous membrane 2 is positioned at the lower side in the direction of gravity G.

Step (B): culturing the first cells 11 at the lower surface of the porous membrane 2 and culturing second cells 12 at the upper surface of the porous membrane 2 in a state in which the porous membrane 2 is held, by the holding member 4, at a position that does not contact the inner bottom surface of the culture vessel 6 so as to face the inner bottom surface, and in which the bottom portion of the culture vessel 6 is positioned at the lower side while the porous membrane 2 is positioned at the upper side in the direction of gravity G.

The term "culture" in the present disclosure does not necessarily involve proliferation of cells, and maintaining of cells in the living state is included in scope of this term regardless of the presence or absence of proliferation.

In the state adopted in the step (A), the bottom portion of the culture vessel 6 is positioned at the upper side while the porous membrane 2 is positioned at the lower side in the direction of gravity G. In the step (A), a cell suspension containing the first cells 11 is provided between the culture vessel 6 and the porous membrane 2 such that the cell suspension contacts the inner bottom surface of the culture vessel 6 and the surface of the porous membrane 2, and the first cells 11 are cultured in this state. Due to the surface tension acting between the inner bottom surface of the culture vessel 6 and the liquid medium contained in the cell suspension, the liquid medium is retained on the porous membrane 2, and falling of the liquid medium through pores in the porous membrane 2 is suppressed. Therefore, a porous membrane having a high aperture ratio can be used as the porous membrane 2 for the production of a cell laminate. The porous membrane 2 is preferably held, by the holding member 4, at a position near the inner bottom surface of the culture vessel 6 in a state in which the porous membrane 2 faces the inner bottom surface of the culture vessel 6 and is oriented parallel to or substantially parallel to the inner bottom surface of the culture vessel 6. The distance between the porous membrane 2 and the inner bottom surface of the culture vessel 6 is, for example, 0.5 mm to 10 mm.

In the step (A), the first cells 11 in the liquid medium migrates in the direction of gravity G due to their own weights, and adhere to the porous membrane 2. The step (A) is a step of adherent-culturing the first cells 11 on the porous membrane 2.

General cell culture conditions may be applied as the cell culture conditions in the step (A). For example, culturing in an incubator at a temperature of 37° C. and a $CO_2$ concentration of 5% (v/v) is applied. The culture period is preferably a period until the adhesion of the first cells 11 to the porous membrane 2 becomes stable.

In the state adopted in the step (B), the bottom portion of the culture vessel 6 is positioned at the lower side while the porous membrane 2 is positioned at the upper side in the direction of gravity G. In the step (B), the first cells 11 are cultured at the lower surface of the porous membrane 2, and the second cells 12 are cultured at the upper surface of the porous membrane 2. The first cells 11 to be cultured at the lower surface of the porous membrane 2 are the first cells 11 that have been cultured in the step (A) on the surface of the porous membrane 2 located at a side facing the inner bottom surface of the culture vessel 6, and the cells are subsequently cultured in the step (B).

General cell culture conditions may be applied as the cell culture conditions in the step (B). For example, culturing in an incubator at a temperature of 37° C. and a $CO_2$ concentration of 5% (v/v) is applied. The culture period is preferably a period until the cells reach confluence on both surfaces of the porous membrane 2. Whether the cells reached confluence can be determined, for example, by observation under an optical microscope. The medium may be changed to another medium during the culture period.

Figure 4:
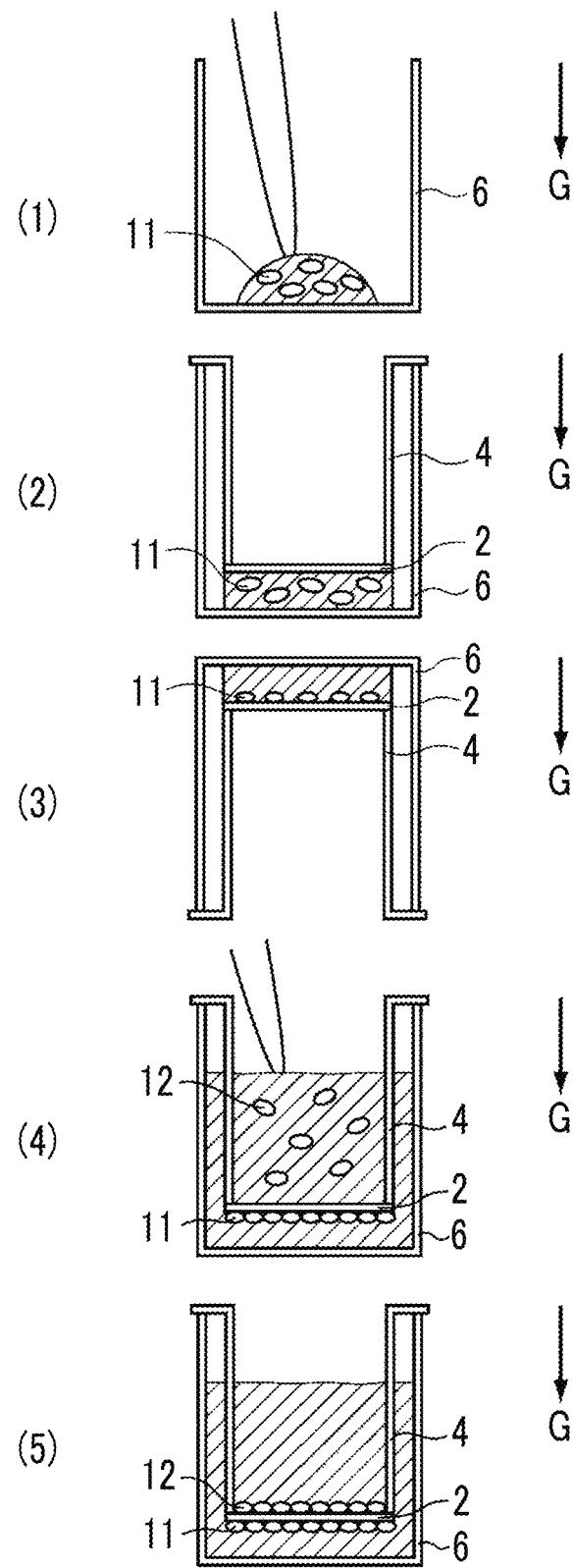
FIG. 4 is a schematic diagram showing an example of the production method of the present disclosure.

One embodiment of the production method of the present disclosure will be described with reference to FIG. 4. The embodiment illustrated in FIG. 4 is a production method using a culture device having a shape illustrated in FIG. 2B. Headings (1) to (5) in FIG. 4 correspond to the following steps (1) to (5), respectively. In FIG. 4, the arrow G indicates the direction of gravity. According to the embodiment including the steps (1) to (5), the production method of the present disclosure can be easily realized.

Step (1): providing a cell suspension containing the first cells 11 on the inner bottom surface of the culture vessel 6.

In the step (1), it is preferable that the cell suspension is provided on the inner bottom surface so as not to contact the inner side surface of the culture vessel 6. This is because it is desired to prevent the cell suspension from falling along the inner side surface of the culture vessel 6 in the step (3). Another means for preventing the cell suspension from falling along the inner side surface of the culture vessel 6 is, for example, setting the size of the porous membrane 2 on its main surface to a size that contacts the inner side surface of the culture vessel 6 over the entire circumference.

In the step (1), the amount of the cell suspension provided on the inner bottom surface of the culture vessel 6 is preferably an amount equivalent to the volume of the space sandwiched between the inner bottom surface of the culture vessel 6 and the porous membrane 2. The seeding density of the first cells 11 is, for example, $1.0 \times 10^3$ to $1.0 \times 10^6$ cells/cm$^2$ with respect to the area of the porous membrane 2.

Step (2): disposing the holding member 4 comprising the porous membrane 2 in the culture vessel 6, and bringing the porous membrane 2 into contact with the cell suspension provided on the inner bottom surface of the culture vessel 6.

As a result of carrying out the step (2), the cell suspension containing the first cells 11 becomes to contact the inner bottom surface of the culture vessel 6 and the surface of the porous membrane 2 (in other words, the cell suspension becomes to be sandwiched between the inner bottom surface of the culture vessel 6 and the surface of the porous membrane 2). Hereinafter, in the description of the production method, the device in which the holding member 4 comprising the porous membrane 2 and the culture vessel 6 are integrated is referred to as a "culture device".

Step (3): culturing the first cells 11 in the liquid medium in contact with the inner bottom surface of the culture vessel 6 and the surface of the porous membrane 2, in a state in which the bottom portion of the culture vessel 6 is positioned at the upper side while the porous membrane 2 is positioned at the lower side in the direction of gravity G.

The step (3) is realized by turning the culture device upside down while the holding member 4 comprising the porous membrane 2 is still installed in the culture vessel 6, and then leaving the culture device to stand still in an incubator. The first cells 11 contained in the cell suspension migrate in the direction of gravity G due to their own weights and adhere to the porous membrane 2.

Step (4): seeding second cells 12 on the upper surface of the porous membrane 2, in a state in which the bottom portion of the culture vessel 6 is positioned at the lower side while the porous membrane 2 is positioned at the upper side in the direction of gravity G.

The step (4) is realized by taking the culture device out of the incubator and turning the culture device upside down again, and then seeding a cell suspension containing the second cells 12 on the porous membrane 2. The seeding density of the second cells 12 is, for example, $1.0 \times 10^3$ to $1.0 \times 10^6$ cells/cm$^2$. A liquid medium is preferably added to the first cells 11 side, before or after the seeding of the second cells 12.

Step (5): culturing the first cells 11 on the lower surface of the porous membrane 2 and culturing the second cells 12 on the upper surface of the porous membrane 2, in a state in which the bottom portion of the culture vessel 6 is positioned at the lower side and the porous membrane 2 is positioned at the upper side in the direction of gravity G.

The step (5) is realized by, subsequent to the step (4), leaving the culture device to stand still in an incubator. The medium may be changed to another medium during the period of the step (5). In a case where at least one of the first cells 11 or the second cells 12 is stem cells, a differentiation-inducing factor that induces differentiation into desired somatic cells is added to the medium.

Through the steps (1) to (5), a cell laminate comprising the porous membrane 2, a cell layer containing the first cells 11 and disposed on one surface of the porous membrane 2, and a cell layer containing the second cells 12 and disposed on the other surface of the porous membrane 2 is obtained.

Hereinafter, the cells for use in the method for producing a cell laminate according to the present disclosure will be described.

The first cells and the second cells may be the same type of cells or different types of cells. A combination of the cell types is selected in accordance with the living tissue to be mimicked by the cell laminate of the present disclosure.

In one embodiment of the production method of the present disclosure, the first cells and the second cells are different types of cells. The two types of cells of the first cells and the second cells are, for example, two types of cells selected from the group consisting of parenchymal cells (for example, hepatic parenchymal cells or pancreatic parenchymal cells), stromal cells (for example, pericytes), myocytes (for example, smooth muscle cells, cardiomyocytes, or skeletal muscle cells), fibroblasts, nerve cells, endothelial cells (for example, vascular endothelial cells or lymphatic endothelial cells) and epithelial cells (for example, alveolar epithelial cells, oral epithelial cells, bile duct epithelial cells, intestinal epithelial cells, pancreatic duct epithelial cells, kidney epithelial cells, renal tubular epithelial cells, or placental epithelial cells), and cells capable of differentiating into any of these cells (for example, progenitor cells, mesenchymal stem cells, or pluripotent stem cells).

Examples of pluripotent stem cells that may be used as the first cells or the second cells include embryonic stem cells (ES cells), induced pluripotent stem cells (iPS cells), embryonic germ cells (EG cells), embryonal carcinoma cells (EC cells), multipotent adult progenitor cells (MAP cells), adult pluripotent stem cells (APS cells), and multi-lineage differentiating stress enduring cells (Muse cells). In the step (B) of the production method according to the present disclosure, a differentiation-inducing factor that induces differentiation into the desired somatic cells is added to the medium, thereby differentiating the pluripotent stem cells into the somatic cells.

In the production method of the present disclosure, a different type of cells (referred to as the "third cells", which may be of one type or plural types) from the first cells and the second cells may be co-cultured with at least one of the first cells or the second cells. As a result of the co-culturing, a cell layer containing the third cells together with the first or second cells is formed on one surface or both surfaces of the porous membrane. For example, the first cells are parenchymal cells, the second cells are stromal cells, and the third cells are nerve cells.

In the production method of the present disclosure, the combination of the first cells and the second cells is selected, and further, the third cells are selected, if necessary, in accordance with the tissue in a living organism to be mimicked, whereby a tissue model mimicking the tissue in a living organism is obtained. In animal tissues, a basement membrane is generally present between one cell layer and another cell layer. In the tissue model obtained by the production method of the present disclosure, the porous membrane corresponds to the basement membrane.

Cells having a genetic mutation or cells derived from a patient may be used as at least one of the first cells or the second cells, with a view to reproducing a disease state.

In one embodiment of the production method of the present disclosure, the first cells are smooth muscle cells or cells capable of differentiating into smooth muscle cells, and the second cells are vascular endothelial cells or cells capable of differentiating into vascular endothelial cells. The production method of the present embodiment provides a cell laminate in which a vascular endothelial cell layer is disposed on one surface of a porous membrane, and a smooth muscle cell layer is disposed on the other surface of the porous membrane, that is, provides a vascular wall model.

The liquid medium to be used for the preparation of a cell suspension or cell culture is selected in accordance with the type of the cells of interest. Specific examples of the media include media optimized for the cell type by adding cell growth factors to a basal medium for mammalian cells, such as Dulbecco's modified Eagle's medium (DMEM), Dulbecco's modified Eagle medium: nutrient mixture F-12 (DMEM: F-12), Eagle's minimal essential medium (EMEM), minimum essential medium alpha (MEMα), and basal medium Eagle (BME). These media are commercially available. The liquid medium may be a medium obtained by mixing a plurality of media, in accordance with the types of cells to be co-cultured. The pH of the liquid medium is, for example, 7.0 to 8.0. The liquid medium preferably has a specific gravity and a viscosity that allow cells to migrate in the direction of gravity due to their own weights.

The method for producing a cell laminate according to the present disclosure enables to obtain a cell laminate comprising:
a porous membrane;
a first cell layer disposed on one surface of the porous membrane; and
a second cell layer disposed on the other surface of the porous membrane.

In the method for producing a cell laminate according to the present disclosure, use of a porous membrane having a honeycomb structure as the porous membrane enables to obtain a cell laminate comprising:
a porous membrane having a honeycomb structure;
a first cell layer disposed on one surface of the porous membrane having a honeycomb structure; and
a second cell layer disposed on the other surface of the porous membrane having a honeycomb structure.

In the method for producing a cell laminate according to the present disclosure, a case where a porous membrane having a honeycomb structure is used as the porous membrane, the first cells are smooth muscle cells or cells capable of differentiating into smooth muscle cells, and the second cells are vascular endothelial cells or cells capable of differentiating into vascular endothelial cells enables to obtain a cell laminate (that is, a vascular wall model) comprising:
a porous membrane having a honeycomb structure;
a smooth muscle cell layer disposed on one surface of the porous membrane having a honeycomb structure; and
a vascular endothelial cell layer disposed on the other surface of the porous membrane having a honeycomb structure.

Use of the porous membrane having a honeycomb structure in the production method of the present disclosure provides a more active cell-cell interaction between cells on one surface and cells on the other surface, during cell culture, which in turn enables the production of a cell laminate having a structure and a function close to those of a tissue in a living organism. Therefore, according to the production method of the present disclosure, use of the porous membrane having a honeycomb structure enables the production of a vascular wall model in which cell-cell adhesion of vascular endothelial cells has developed to a state close to that in a vascular wall in a living organism.

The vascular wall model preferably prevents chemical substances from freely passing between cells in a vascular endothelial cell layer, in other words, preferably has a barrier function. In the vascular wall model obtained by the production method of the present disclosure, cell-cell adhesion among vascular endothelial cells has presumably developed to a state close to a vascular wall in a living organism. In order to more accurately evaluate drugs using a vascular wall model, the vascular wall model desirably has a structure and a function similar to those of a vascular wall in a living organism. Therefore, the vascular wall model obtained by the production method of the present disclosure can work as an excellent means for evaluating drugs.

The application of the cell laminate obtained by the production method of the present disclosure is not limited. The cell laminate obtained by the production method of the present disclosure is useful as a material for transplantation into a living organism, a tissue model for evaluating drugs or disease states, or a test tissue that could replace animal testing.

EXAMPLES

Hereinafter, embodiments of the present disclosure will be described with reference to examples, but the embodiments of the present disclosure are not limited to these examples.

In the following description, "M" used in relation to the concentrations of a substance refers to a molar concentration, and 1 M corresponds to 1 mol/L.

Abbreviations of chemical substances used in the examples below are as follows.
EGM: endothelial cell growth medium
FITC: fluorescein isothiocyanate
HBSS: Hanks' balanced salt solution
HCM: honeycomb membrane
HUASMCs: human umbilical artery smooth muscle cells
HUVECs: human umbilical vein endothelial cells
PBS: phosphate buffered saline
TEM: track-etched membrane Example 1

Figure 5:
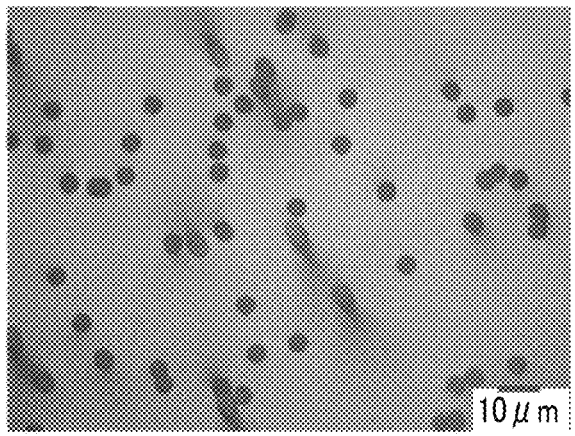
FIG. 5 is a microscopic image of a porous membrane used in Example 1.
Figure 5:
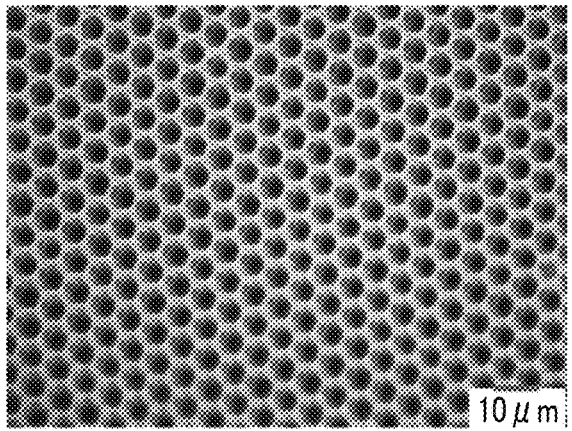

[Cell Culture Equipment]
24-well plate: suspension culture quality (#662-102, Greiner)
TEM insert: 24-well hanging insert (#MCMP24H48, Millipore) comprising a TE membrane in a filter portion. A microscopic image of the TE membrane comprised in the insert is shown in FIG. 5. The TE membrane has an opening diameter of 5.7 μm, a membrane thickness of 10.6 μm, an aperture ratio of 12.4%, and is made of polyethylene terephthalate.
HCM insert: 24-well hanging insert comprising a porous membrane having a honeycomb structure in a filter portion. A microscopic image of the porous membrane comprised in the insert is shown in FIG. 5. The porous membrane has an opening diameter of 5.0 μm, a membrane thickness of 2.2 μm, an aperture ratio of 55%, and is made of polybutadiene.
HCM coating material: fibronectin (#33016-015, Invitrogen)
[Cells]
Vascular endothelial cells: HUVECs (#C2517AS, Lonza)
Smooth muscle cells: HUASMCs (#C-12500, PromoCell)
[Liquid Medium and Cell Detachment Reagent]
EGM-2 (#CC-3162, Lonza) for HUVECs
Smooth Muscle Cell Growth Medium 2 Kit (#C-22162, PromoCell) for HUASMCs
Accutase (AT104-500, Innovative Cell Technologies)

[Sterilization of HCM]

(1) 500 μL/well of 70% (v/v) ethanol was added to wells of one 24-well plate, and 500 μL/well of PBS was added to wells of two other 24-well plates. Separately, a cup to which 70% (v/v) ethanol has been added was prepared.

(2) HCM inserts were passed through the cup containing ethanol, and then the HCM inserts were placed in wells containing ethanol such that their HCMs were immersed in ethanol, and the HCM inserts were left to stand still for 5 minutes.

(3) The HCM inserts were taken out of the ethanol, and ethanol was removed from the inner side of each HCM insert using an aspirator. The HCM inserts were immediately transferred to wells containing PBS and placed such that their HCMs were immersed in PBS. 1 mL of PBS was poured thereto.

(4) The HCM inserts were taken out of the PBS, and PBS was removed from the inner side of each HCM insert using an aspirator. The HCM inserts were immediately transferred to wells containing PBS, and placed such that their HCMs were immersed in PBS. 1 mL of PBS was poured thereto.

(5) The HCM inserts being immersed in PBS were put in a vacuum desiccator, thereby deaerating the HCMs.

(6) The HCM inserts were observed under a microscope to confirm that the HCM inserts were free of breakage, attaching matters and HCM wrinkles.

[Fibronectin Coating of HCM]

(1) Fibronectin was dissolved in PBS to prepare a fibronectin solution having a concentration of 30 μg/mL.

(2) 70 μL of the fibronectin solution was spotted on central portions of wells of a 24 well-plate.

(3) The HCM inserts were taken out of the PBS, and the PBS was removed from the inner side of each HCM insert using an aspirator and the HCM inserts were immediately put on the fibronectin solution spots on the wells to immerse their HCMs in the fibronectin solution.

(4) 100 μL of the fibronectin solution was poured to the inner side of each HCM insert, and the HCM inserts were left to stand still at room temperature for one hour (or left to stand still at 4° C. overnight).

[Cell Culture using HCM Insert (Production of Cell Laminate)]

(1) 80 μL of a cell suspension of HUASMCs was put, in a dome shape, on central portions of wells of a 24-well plate.

(2) The coated HCM inserts were each placed on the cell suspension of HUASMCs, thereby sandwiching the cell suspension between the bottom surface of the well and the HCM.

(3) The plate and the HCM inserts were turned upside down in a state in which the cell suspension was sandwiched between the bottom surface of the well and the HCM. The plate and the HCM inserts in the state of being turned upside down were placed in an incubator (37° C., 5% (v/v) $CO_2$) and culturing was carried out for 16 hours.

(4) 1200 μL of Smooth Muscle Cell Growth Medium 2 Kit was added to the outer side of each HCM insert. The plate and the HCM inserts were taken out of the incubator, the orientation of the plate and the HCM inserts was returned to the initial orientation, and the HCM inserts were transferred to wells that contained a medium. Thereafter, 300 μL of a cell suspension of HUVECs was seeded in the inner side of each HCM insert.

(5) The plate and the HCM inserts were put in an incubator (37° C., 5% (v/v) $CO_2$), and culturing was carried out for 80 hours.

The seeding conditions for the respective types of cells were as follows.

HUASMCs: the culture area was 0.785 $cm^2$, the seeding density was $1.0 \times 10^4$ cells/$cm^2$, and the volume of the cell suspension was 80 μL.

HUVECs: the culture area was 0.32 $cm^2$, the seeding density was $5.0 \times 10^4$ cells/$cm^2$, and the volume of the cell suspension was 300 μL.

Figure 6:
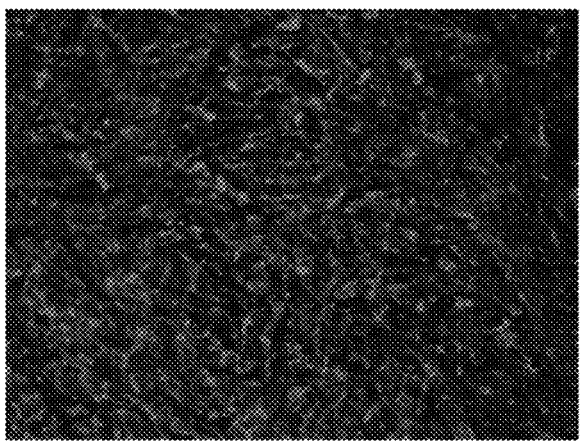
FIG. 6 is an immunofluorescence-stained image of each of cell layers formed on both surfaces of the porous membrane in Example 1.
Figure 6:
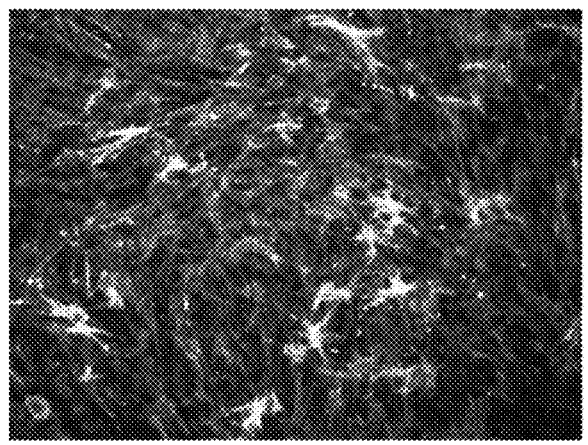

As a result of the above culture, an HCM insert in which a vascular endothelial cell layer was disposed on the upper surface of the filter, and a smooth muscle cell layer was disposed on the lower surface of the filter (referred to as the "VEC/SMC-HCM insert") was obtained. The cell layer on the upper surface immunofluorescence-stained for CD31, and the cell layer on the lower surface immunofluorescence-stained for α-smooth muscle actin are shown in FIG. 6.

In a manner similar to the above procedures, an HCM insert in which a vascular endothelial cell layer was disposed on the upper surface of the filter and no cell layer was disposed on the lower surface of the filter (referred to as the "VEC-HCM insert"), and an HCM insert in which a smooth muscle cell layer was disposed on the lower surface of the filter and no cell layer was disposed on the upper surface of the filter (referred to as the "SMC-HCM insert") were prepared.

[Cell Culture using TEM Insert (Production of Cell Laminate by Conventional Method)]

In a state in which the TEM inserts were placed upside down, HUASMCs were seeded on their filters, the TEM inserts were put in an incubator (37° C., 5% (v/v) $CO_2$), and culturing was carried out for 16 hours. Then, the TEM inserts were placed in wells of a 24-well plate, HUVECs were seeded in the inner side of each TEM insert, and 1200 μL of Smooth Muscle Cell Growth Medium 2 Kit was added to the outer side of each TEM insert. Then, the TEM inserts were put in an incubator (37° C., 5% (v/v) $CO_2$) and culturing was carried out for 80 hours.

The conditions for seeding cells into the TEM inserts were the same as the conditions for seeding the cells into the HCM inserts.

As a result of the above culture, a TEM insert in which a vascular endothelial cell layer was disposed on the upper surface of the filter and a smooth muscle cell layer was disposed on the lower surface of the filter (referred to as the "VEC/SMC-TEM insert") was obtained.

In a manner similar to the above procedures, a TEM insert in which a vascular endothelial cell layer was disposed on the upper surface of the filter and no cell layer was disposed on the lower surface of the filter (referred to as the "VEC-TEM insert"), and a TEM insert in which a smooth muscle cell layer was disposed on the lower surface of the filter and no cell layer was disposed on the upper surface of the filter (referred to as the "SMC-TEM insert") were prepared.

[Evaluation of Substance Permeability]

(1) 2 mg of FITC-dextran 70 (70 kDa, Sigma) was dissolved in 8 mL of HBSS(+) (084-08965, Wako Pure Chemical Industries, Ltd.) to prepare a FITC-dextran 70 solution having a concentration of 250 μg/mL. The FITC-dextran 70 solution was stored in a light-shielded condition.

(2) 900 μL/well of HBSS(+) was added to each of the wells in the first to third columns of a 24-well plate.

(3) Inserts comprising a cell laminate were taken out of the medium, and medium was removed from the inner side of each insert using an aspirator. The inserts were placed in wells in the first column.

(4) 200 μL of the FITC-dextran 70 solution was added to the inner side of each of the inserts put in the wells in the first column, followed by incubation at 37° C. for 10 minutes.

(5) The inserts were transferred to wells in the second column, and incubated at 37° C. for 10 minutes.

(6) The inserts were transferred to wells in the third column and immediately light-shielded by covering the plate with an aluminum sheet.

(7) Each of the sample liquids in the wells in the first and second columns was mixed using a pipette, and 100 μL of the sample liquid was sampled from each of the wells and transferred to a 96-well black plate. The 96-well black plate was light-shielded by covering the plate with an aluminum sheet.

(8) The fluorescence intensity of the FITC in each sample liquid was measured using a plate reader (EnSpire, PerkinElmer) with Ex/Em=485 nm/530 nm and the number of light irradiations of 60 times.

Figure 7:
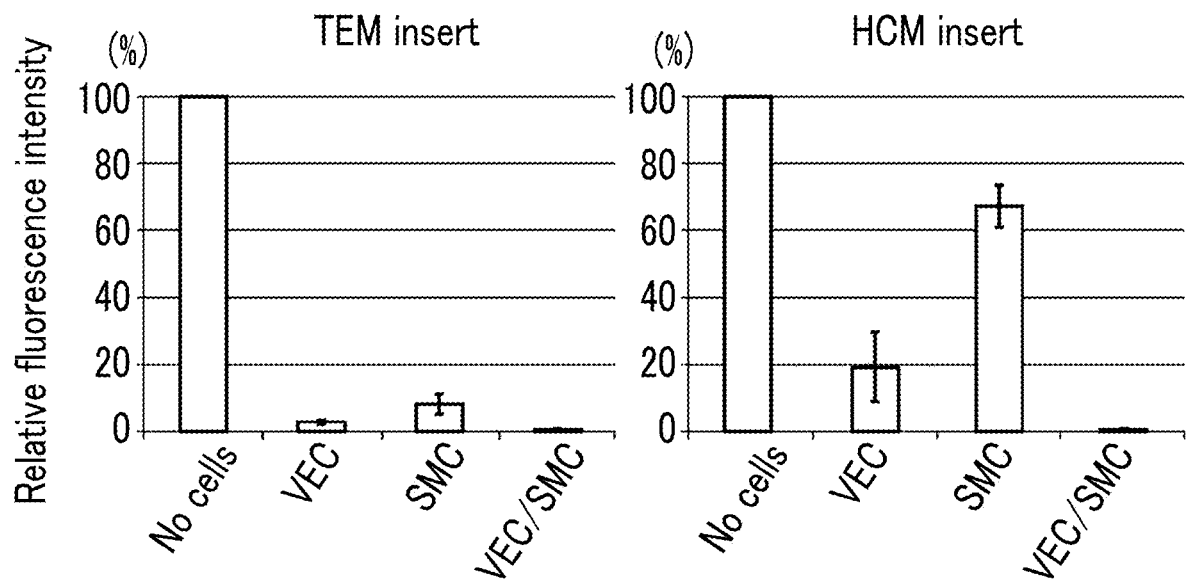
FIG. 7 is a graph showing a relative fluorescence intensity of FITC-dextran 70.

The relative fluorescence intensity of the FITC in the sample liquids (that is, the relative amount of FITC-dextran 70 that leaked within 10 minutes from the addition of the FITC-dextran 70 solution) in the wells in the first column is shown in FIG. 7. The graph in FIG. 7 shows the relative fluorescence intensity based on the fluorescence intensity in the insert in which the cell layer is not formed on both surfaces of the filter.

In the case of the TEM inserts, the VEC-TEM inserts exhibited a relative fluorescence intensity of 3.0±0.5% (n=5), the SMC-TEM inserts exhibited a relative fluorescence intensity of 8.2±2.9% (n=5), and the VEC/SMC-TEM inserts exhibited a relative fluorescence intensity of 0.4±0.2% (n=5). The relative fluorescence intensity of the SMC-TEM inserts was the above-noted value although smooth muscle cell layers in general do not have highly tight cell-cell bonding. Therefore, this result presumably indicates that the TEM itself carries out a barrier function against FITC-dextran 70 in the TEM inserts.

In the case of the HCM inserts, the VEC-HCM inserts exhibited a relative fluorescence intensity of 19.3±10.2% (n=5), the SMC-HCM inserts exhibited a relative fluorescence intensity of 67.4±6.1% (n=5), and the VEC/SMC-HCM inserts exhibited a relative fluorescence intensity of 0.4±0.3% (n=5). The barrier function against FITC-dextran 70 was acquired by forming a vascular endothelial cell layer on one surface of an HCM, and forming a smooth muscle cell layer on the other surface of the HCM.

Example 2

[Cell Culture Equipment]
  24-well plate: suspension culture quality (#662-102, Greiner)
  HCM insert: 24-well hanging insert comprising a porous membrane having a honeycomb structure in a filter portion. The porous membrane has an opening diameter of 3.0 μm, a membrane thickness of 1.2 μm, an aperture ratio of 55%, and is made of polycarbonate.
  HCM coating material: collagen I rat tail (#354236, Corning)
[Cells]
  Vascular endothelial cells: rat vascular endothelial cells (#cAP-r0001, Angio-Proteomie)
  Smooth muscle cells: rat smooth muscle cells (#R-ASM-580, Lonza)
[Liquid Medium and Cell Detachment Reagent]
  Rat endothelial cell growth medium (#cAP-03, cAP-04, Angio-Proteomie) for rat vascular endothelial cells
  DMEM: F-12 (1:1) medium (#BE04-687Q, Lonza) for rat smooth muscle cells
  Accutase (AT104-500, Innovative Cell Technologies)

[Sterilization of HCM]
HCM was sterilized in the same manner as in Example 1.
[Collagen Coating of HCM]
(1) Collagen I was dissolved in a 0.2 N acetic acid solution to prepare a collagen I solution having a concentration of 50 μg/mL.

(2) 70 μL of the collagen I solution was spotted on central portions of wells of a 24-well plate.

(3) The HCM inserts were taken out of PBS, the PBS was removed from the inner side of each HCM insert using an aspirator, and the HCM inserts were immediately put on the collagen I solution spots on the wells to immerse their HCMs in the collagen I solution.

(4) 100 μL of the collagen I solution was poured to the inner side of each HCM insert, and the HCM inserts were left to stand still at room temperature for 4 hours (or left to stand still at 4° C. overnight).

(5) 500 μL of PBS was added to neutralize the HCMs.
[Cell Culture using HCM Instert (Production of Cell Laminate)]
(1) 80 μL of a cell suspension of rat smooth muscle cells was put, in a dome shape, on central portions of wells of a 24-well plate.

(2) The coated HCM inserts were each placed on the cell suspension of rat smooth muscle cells, thereby sandwiching the cell suspension between the bottom surface of the well and the HCM.

(3) The plate and the HCM inserts were turned upside down in a state in which the cell suspension was sandwiched between the bottom surface of the well and the HCM. The plate and the HCM inserts in the state of being turned upside down were placed in an incubator (37° C., 5% (v/v) $CO_2$) and culturing was carried out for 16 hours.

(4) 1200 μL of a rat endothelial cell growth medium was added to the outer side of each HCM insert. The plate and the HCM inserts were taken out of the incubator, the orientation of the plate and the HCM inserts was returned to the initial orientation, and the HCM inserts were transferred to wells that contained a medium. Thereafter, 300 μL of a cell suspension of rat vascular endothelial cells was seeded in the inner side of each HCM insert.

(5) The plate and the HCM inserts were put in an incubator (37° C., 5% (v/v) $CO_2$), and culturing was carried out for 80 hours.

The seeding conditions for the respective types of cells were as follows.
  Rat smooth muscle cells: the culture area was 0.785 $cm^2$, the seeding density was $1.0 \times 10^4$ cells/$cm^2$, and the volume of the cell suspension was 80 μL.
  Rat vascular endothelial cells: the culture area was 0.32 $cm^2$, the seeding density was $5.0 \times 10^4$ cells/$cm^2$, and the volume of the cell suspension was 300 μL.

As a result of the above culture, an HCM insert in which a vascular endothelial cell layer was disposed on the upper surface of the filter, and a smooth muscle cell layer was disposed on the lower surface of the filter (referred to as the "VEC/SMC-HCM insert") was obtained. The cell layer on the upper surface immunofluorescence-stained for VE-cadherin, and the cell layer on the lower surface immunofluorescence-stained for calponin are shown in FIG. 8.

Figure 8:
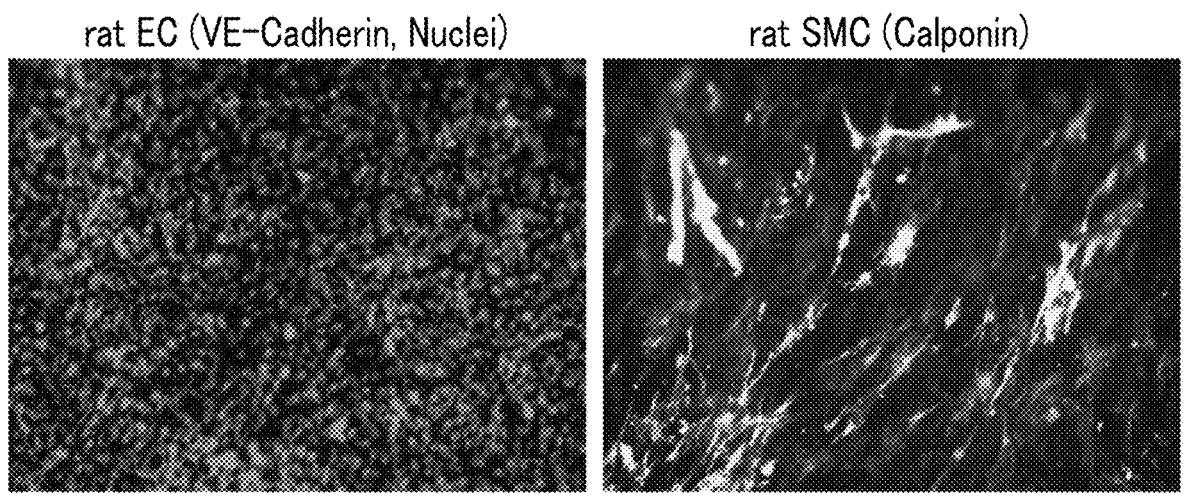
FIG. 8 is an immunofluorescence-stained image of each of cell layers formed on both surfaces of the porous membrane in Example 2.

As shown in FIG. 8, formation of a confluent cell layer and localization of vascular endothelial cadherin were clearly observed. The localization of vascular endothelial cadherin indicates strong adhesion between vascular endothelial cells (formation of cell-cell junctions), and is one of the characteristics of an actual vascular wall. Thus, a cell laminate having a structure similar to that of a living tissue could be prepared by forming a vascular endothelial cell layer on one surface of the HCM and forming a smooth muscle cell layer on the other surface of the HCM.

[Evaluation of Response to Physiologically Active Substances]

(1) 0.1 mg (100 UN) of thrombin (#T7009-100UN, Sigma) was dissolved in 100 μL of physiological saline to prepare a thrombin solution having a concentration of 1000 U/mL. The thrombin solution was further diluted with HBSS(+) to prepare a 25 U/mL thrombin solution and a 100 U/mL thrombin solution.

(2) 900 μL of HBSS(+) was added to each of the wells of a 24-well plate.

(3) The inserts comprising the cell laminate were taken out of the medium, the medium was removed from the inner side of each insert using an aspirator, and the inserts were placed in the wells.

(4) 200 μL of either HBSS(+) (control), the 25 U/mL thrombin solution, or the 100 U/mL thrombin solution was added to the inner side of each of the inserts placed on the wells, and the inserts were incubated at 37° C. for 30 minutes.

Figure 9:
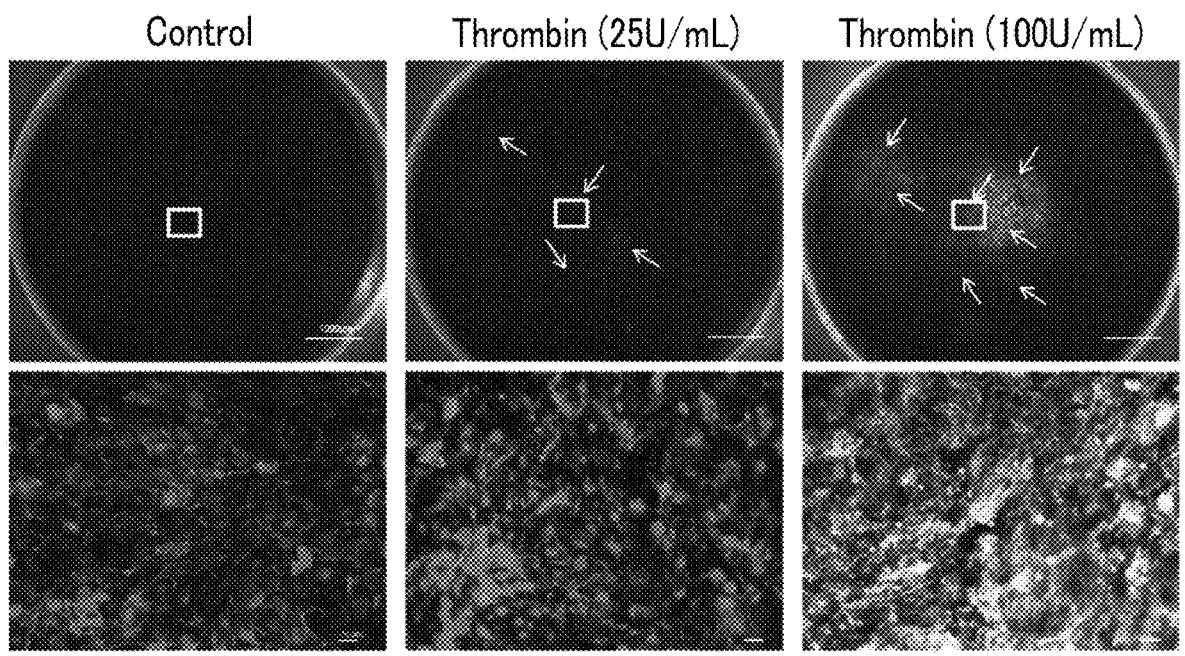
FIG. 9 is an immunofluorescence-stained image of a cell laminate in Example 2.

(5) The state of the cell laminate was observed under a microscope. The microscopic image of the cell laminate is shown in FIG. 9 (superimposed image of red fluorescence: VE-cadherin and green fluorescence: α-smooth muscle actin).

As shown in FIG. 9, cell contraction due to activation of actin stress fibers caused by the addition of thrombin was observed. The cell contraction was observed in the arrow direction shown in the upper portion of FIG. 9. Higher thrombin concentrations caused stronger cell contractions. It was thus confirmed that the cell laminate comprising a vascular endothelial cell layer on one surface of an HCM and comprising a smooth muscle cell layer on the other surface of the HCM responses to a physiologically active substance in a manner similar to that exhibited by living tissues.

The disclosure of JP2017-114755 filed on Jun. 9, 2017 is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

EXPLANATION OF REFERENCES

2: porous membrane
4: holding member
6: culture vessel
11: first cell
12: second cell
20: porous membrane
22: through-hole
24: partition wall
40: holding member
42: cylindrical portion
44: protruding portion
60: culture vessel
62: bottom portion
64: side wall portion

What is claimed is:

1. A method for producing a cell laminate comprising cell layers on both surfaces of a porous membrane, using a vessel having a bottom portion and a side wall portion standing from a periphery of the bottom portion, the porous membrane, and a holding member configured to hold the porous membrane such that the porous membrane faces an inner bottom surface of the vessel and is held at a position that does not contact the inner bottom surface, the method comprising:

culturing first cells in a liquid medium that contacts the inner bottom surface of the vessel and a surface of the porous membrane, in a state in which the porous membrane is held, by the holding member, at a position that does not contact the inner bottom surface of the vessel so as to face the inner bottom surface, in which the inner bottom surface of the vessel is above the porous membrane in a direction of gravity, and in which surface tension acts between the inner bottom surface of the vessel and the liquid medium; and culturing the first cells at a lower surface of the porous membrane and culturing second cells at an upper surface of the porous membrane, in a state in which the porous membrane is held, by the holding member, at a position that does not contact the inner bottom surface of the vessel so as to face the inner bottom surface, and in which the inner bottom surface of the vessel is below the porous membrane in the direction of gravity, wherein the porous membrane has an aperture ratio of from 55% to 70%.

2. The method for producing a cell laminate according to claim 1, wherein the inner bottom surface of the vessel has a property that the first cells do not adhere.

3. The method for producing a cell laminate according to claim 1, wherein the holding member comprises:

a cylindrical portion configured to hold the porous membrane at one axial-direction end of the cylindrical portion, the cylindrical portion having a smaller outer diameter than an inner diameter of the vessel, and a length of the cylindrical portion in the axial direction being shorter than a height of the side wall portion of the vessel; and a protruding portion protruding outwardly in a radial direction from the other axial-direction end of the cylindrical portion, the protruding portion being configured to engage with an edge of the side wall portion of the vessel.

4. The method for producing a cell laminate according to claim 1, wherein the porous membrane is a porous membrane having a honeycomb structure.

5. The method for producing a cell laminate according to claim 1, wherein a material of the porous membrane is at least one selected from the group consisting of polybutadiene, polystyrene, polycarbonate, polylactic acid, and a polylactic acid-polyglycolic acid copolymer.

6. The method for producing a cell laminate according to claim 1, wherein, in the porous membrane, at least the surface on which the cells are cultured is coated with at least one selected from the group consisting of fibronectin, collagen, laminin, vitronectin, gelatin, perlecan, nidogen, proteoglycan, osteopontin, tenascin, nephronectin, a basement membrane matrix, and polylysine.

7. The method for producing a cell laminate according to claim 1, wherein the first cells and the second cells are different types of cells, and the two types of cells of the first cells and the second cells are two types of cells selected from the group consisting of parenchymal cells, stromal cells, myocytes, fibroblasts, nerve cells, endothelial cells, epithelial cells, and cells capable of differentiating into any of these cells.

8. The method for producing a cell laminate according to claim 1, wherein the first cells are smooth muscle cells or cells capable of differentiating into smooth muscle cells, and the second cells are vascular endothelial cells or cells capable of differentiating into vascular endothelial cells.

* * * * *